(12) United States Patent
Peppas et al.

(10) Patent No.: US 8,940,394 B2
(45) Date of Patent: Jan. 27, 2015

(54) PROTEIN IMPRINTING BY MEANS OF ALGINATE-BASED POLYMERS

(75) Inventors: Nicholas A. Peppas, Austin, TX (US); Edgar Perez-Herrero, Salamanca Province (ES)

(73) Assignee: Board of Regents, The University of Texas System, Austin, TX (US)

( * ) Notice: Subject to any disclaimer, the term of this patent is extended or adjusted under 35 U.S.C. 154(b) by 121 days.

(21) Appl. No.: 13/419,875

(22) Filed: Mar. 14, 2012

(65) Prior Publication Data

US 2012/0276386 A1    Nov. 1, 2012

Related U.S. Application Data

(63) Continuation-in-part of application No. PCT/US2010/048718, filed on Sep. 14, 2010.

(60) Provisional application No. 61/241,994, filed on Sep. 14, 2009.

(51) Int. Cl.
*C08L 5/04* (2006.01)
*C08L 89/00* (2006.01)
*A61K 9/50* (2006.01)
*A61K 38/00* (2006.01)

(52) U.S. Cl.
CPC .......... *A61K 9/5036* (2013.01); *A61K 9/5089* (2013.01); *A61K 38/00* (2013.01)
USPC ............... 428/402; 428/402.2; 106/144.1; 106/205.01

(58) Field of Classification Search
USPC ......... 428/402–402.24, 403, 404, 407, 321.1, 428/474.4; 427/331, 389.9, 212, 427/213–213.36, 483, 256; 264/534, 5, 41, 264/4–4.7; 106/144.1, 205.01
See application file for complete search history.

(56) References Cited

PUBLICATIONS

Zhang et al., Reactive & Functioanl Polymers 66 (2006) 712-719.*
Zhao e tal., Reactive & Functioanl Polymers 68 (2008) 732-741.*
Zhang, et al., "Emulsion and macromolecules templated alginate based polymer microspheres," Jul. 2006, Reactive & Functional Polymers, vol. 66, Is. 7, pp. 712-719, especially p. 713, col. 2, para 1-4; p. 714, col. 1, para 2-5 and col. 2, para 3-4; p. 715, col. 2, para 5; p. 716, col. 1, para 2 to col. 2, para 1; and p. 717, col. 2, para 1.
Ghosh, et al., "A study on the effect of different acrylic polymers on Frusemide loaded calcium alginate micropellets prepared by ionotropic gelation technique," Pharmacy On-Line: The International Forum for Pharmacy [online], Apr. 2007, [retrieved on Oct. 12, 2010]. Retrieved from the internet: <URL: http://www.priory.com/pharmol/microspheres.htm]; p. 1-10, especially p. 2, para 5; p. 4, para 5; and p. 5, para 7.
Zhao, et al., "Rebinding and recognition properties of protein-macromolecularly imprinted calcium phosphate/alginate hybrid polymer microspheres," Mar. 2008, Reactive & Functional Polymers, vol. 68, Is. 3, pp. 732-741, especially p. 733, col. 2, para 3; p. 734, col. 1, para 2; p. 735, col. 1, para 1; and p. 738, col. 1, para 1.

(Continued)

*Primary Examiner* — James J Seidleck
*Assistant Examiner* — S. Camilla Pourbohloul
(74) *Attorney, Agent, or Firm* — Reed Smith LLP; Robert R. Riddle

(57) ABSTRACT

Methods of preparing molecularly imprinted polymers are provided. In one embodiment, a method comprises providing a solution comprising a template molecule; and forming a product comprising calcium alginate in the presence of the template molecule so that the template molecule is imprinted in the product.

14 Claims, 15 Drawing Sheets

(56) References Cited

PUBLICATIONS

Herrero, et al., "Develoment of a new technology for the production of microcapsules based on atomization processes," Apr. 2006, Chemical Engineering Journal, vol. 117, Is. 2, pp. 137-142, especially p. 138, col. 2, para 3; and p. 141, col. 2, para 4-6.

Herrero, et al., "Protein Imprinting by Means of Alginate-Based Polymer Microcapsules," Industrial & Engineering Chemical Research [online], Aug. 19, 2010, [retrieved on Oct. 11, 2010]. Retrieved from the Internet: <URL: http://pubs.acs.org/doi/abs/10.1021/ie101068z]; entire document.

International Search Report for PCT/US2010/48718 dated Oct. 12, 2010.

International Preliminary Report on Patentability for PCT/US2010/48718 dated Mar. 20, 2012.

* cited by examiner

PROTEIN IMPRINTING BY MEANS OF ALGINATE-BASED POLYMERS

CROSS REFERENCE TO RELATED APPLICATIONS

This application is a continuation in part of International Patent Application No. PCT/US10/48718 filed Sep. 14, 2010 and claims priority to U.S. Provisional Application No. 61/241,994, filed Sep. 14, 2009, both of which are incorporated herein by reference.

BACKGROUND

The present invention relates to molecular imprinting polymers, and, at least in some embodiments, to novel calcium alginate polymer microcapsules and films, and their associated methods of use.

A molecular imprinting polymer ("MIP") is generally a crosslinked polymeric network formed in the presence of an imprinting compound or "template molecule" such that the template molecule may be later removed, leaving a MIP that is able to recognize and bind to the template molecule via a complementary binding cavity. The release of the template molecule allows the MIP material to exhibit a selective "memory" with respect to the template molecule. This simulates the typical molecular recognition of biological systems, such as antibodies or enzymes. MIPs tend to show a certain chemical affinity for the original template molecule and, consequently, can be used to fabricate sensors, as catalysis, or for separation methods.

Molecular imprinting has been successfully used to recognize small molecules, such as herbicides, metal ions, and amino acids. Thus, MIPs can be used as sensors, chromatography beds, resins for separation processes, and analytical tools in enzyme-linked immunosorbent assays ("ELISA assays").

Heretofore, bio-macromolecules, such as antibodies and enzymes, have been employed for protein recognition purposes. However, such bio-macromolecules are sometimes difficult to find and/or produce. Thus, there is a need for receptor-like synthetic materials such as protein-imprinted polymers as substitutes for natural receptors.

However, the development of MIPs capable of recognizing macromolecules, such as peptides and proteins, has met with many difficulties. The current approach to macromolecular imprinting generally involves the inclusion of a template molecule within a polymer formed from functional monomers and crosslinking agents. However, macromolecular imprinting technologies heretofore have been generally incompatible with the diagnosis and recognition in many life sciences applications, such as medical applications, food additives, or drug delivery, which require biocompatible or alimentary products.

Alginate is generally a water soluble linear polysaccharide derived from brown algae and composed of alternating blocks of 1,4' linked α-L-guluronic and β-D-mannuronic acid residues (FIG. 9). Physical networks are formed by the exchange of sodium ions associated with the guluronic acid residues with divalent cations in the cross-linking solutions. The guluronic residues stack to form a characteristic egg-box structure. Dimerization of the alginate chains occurs through the divalent cations, as illustrated in FIG. 10, causing junctions between many chains to create a network structure. Although the biocompatibility and biodegradability of alginates has been documented, only limited studies have been done using alginate microcapsules to achieve macromolecular imprinting. In fact, it is believed that each of the works to date have used the inverse suspension method to produce alginate microcapsules, which involves the use of organic chemicals, such us chloroform and hexane, that are incompatible with the medical and alimentary purposes. Similarly, such attempts have been able to achieve at most a recognition of between about 0.46 mg to about 0.66 mg of the template molecule bovine serum albumin ("BSA") per gram of microcapsule. In addition, in these works, typically at least 48 hours has been required to achieve the release of the template molecule.

SUMMARY

The present invention relates to molecular imprinting polymers, and, at least in some embodiments, to novel calcium alginate polymer microcapsules and films, and their associated methods of use.

The features and advantages of the present invention will be apparent to those skilled in the art. While numerous changes may be made by those skilled in the art, such changes are within the spirit of the invention.

DRAWINGS

These drawings illustrate certain aspects of some of the embodiments of the present invention, and should not be used to limit or define the invention.

FIG. 1 illustrates a method of macromolecular imprinting according to one embodiment of the invention.

FIG. 2 is a graph illustrating the amount of template molecule (BSA) released from the calcium alginate microcapsules over a series of steps. The removal process was carried out in the following steps: 1. Mixing=3 h 4'/Continuous=1 h 42', 2. Mixing=2 h 30'/Continuous=20', 3. Mixing=35'/Continuous=9', 4. Filtering, 5. Stored=1 d, 6. Stored=1 d. The initial amount of BSA removed was 21.8618 mg. The final amount of BSA remaining was 2.1784 mg, for a total template removal of 90.04%.

FIG. 3 is a graph illustrating the amount of template molecule (BSA) released from the calcium alginate microcapsules over a series of steps. The removal process was carried out in the following steps: 1. Mixing=2 h 28'/Continuous=30', 2. Mixing=1 h 40'/Continuous=10', 3. Mixing=40'/Continuous=8', 4. Filtering, 5. Stored=1 d, 6. Stored=1 d. The initial amount of BSA removed was 22.6153 mg. The final amount of BSA remaining was 2.9145 mg, for a total template removal of 87.11%.

FIG. 4 is a graph illustrating the amount of template molecule (BSA) released from the calcium alginate microcapsules over a series of steps (total release, overnight mixing). The removal process was carried out in the following steps: 1. Mixing=2 h 30'/Continuous=30', 2. Mixing=4 h 30'/Continuous=22', 3. Mixing=Overnight (12 h 48'),/Continuous=13'. The initial amount of BSA removed was 22.4844 mg. The final amount of BSA remaining was 0 mg, for a total template removal of 100%.

FIG. 5 is a graph illustrating the amount of template molecule (BSA) released from the calcium alginate microcapsules over a series of steps (total release, 5 days of storage in DI water). The removal process was carried out in the following steps: 1. Mixing=3 h 4'/Continuous=1 h 42', 2. Mixing=2 h 30'/Continuous=20', 3. Stored=3 d, 4. Stored=1 d, 5. Stored=1 d. The initial amount of BSA removed was 23.3631 mg. The final amount of BSA remaining was 0.0604 mg, for a total template removal of 97.74%.

Figure 13:
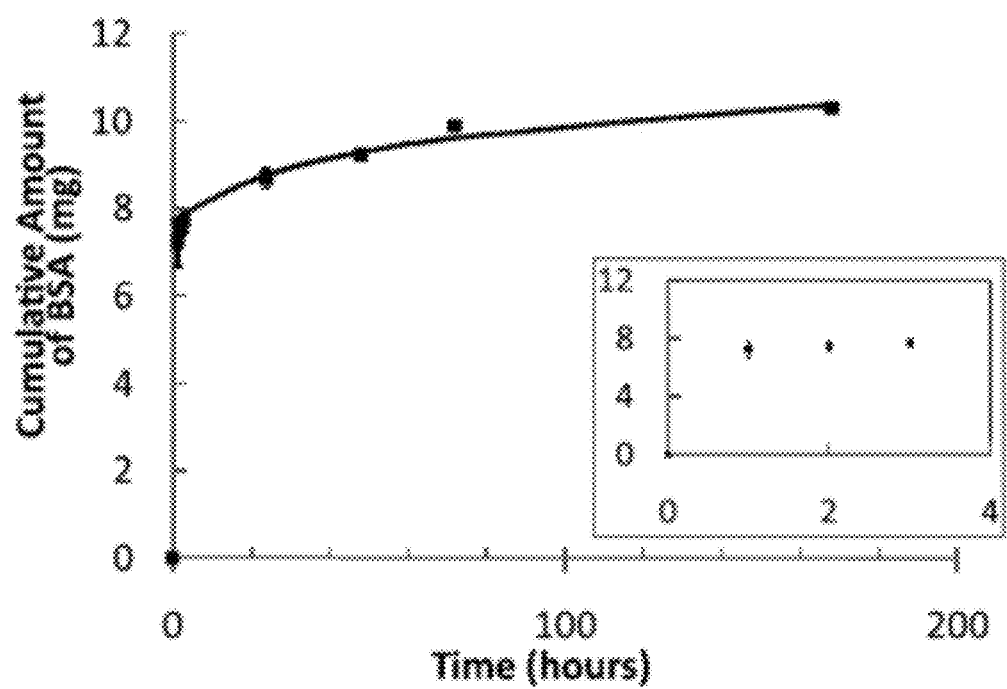

FIG. 13 shows cumulative amount of BSA released from the imprinted alginate film during 0.05 M Tris-HCl (pH 7.5) with 1% $CaCl_2$ rinse (hours 1, 2 and 3, shown in detail in inset) and during deionized water rinse (remaining timepoints) (n=3). Error bars represent ±1 SD. Exponential fit to data is shown.

Figure 14:
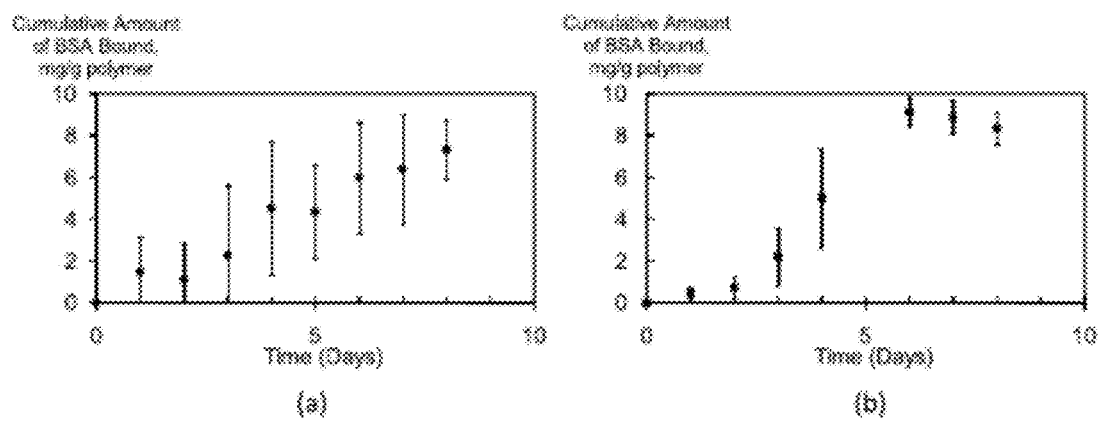

FIG. 14 shows cumulative absorption of BSA into imprinted alginate films: (a) as an average (n=4) of four separate imprinting and recognition replicates and (b) single replicate demonstrating attainment of equilibrium after 6 days. Error bars delineate ±1 SD.

Figure 15:
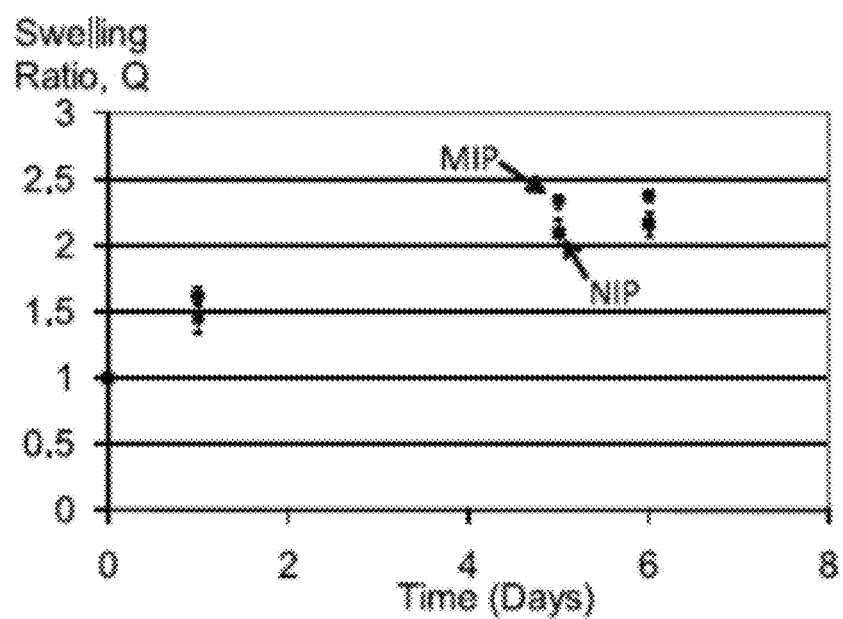

FIG. 15 shows swelling of imprinted and non-imprinted alginate films. A similar degree of swelling is seen in both types of films, regardless of whether cross-linking occurred in the presence of BSA (n=6).

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present invention relates to molecular imprinting polymers, and, at least in some embodiments, to novel calcium alginate polymer microcapsules, and their associated methods of use.

In accordance with embodiments of the present invention, methods of the present invention may provide new means of protein imprinting and new techniques of generation of calcium alginate-based polymer microcapsules which are compatible with life sciences applications—such as medical diagnosis, detection in the food industry, or drug delivery—requiring biocompatible or alimentary products. One of the many potential advantages of the methods of the present invention, only some of which are herein disclosed, is that these methods may be capable of recognizing a higher quantity of template molecule than existing technologies, with a simple formulation and with biocompatible materials. For example, the materials used in many embodiments of the invention, sodium alginate and calcium chloride, may be totally biocompatible with the medical and food industry.

Some embodiments of the invention provide macromolecular imprinting using calcium alginate based polymer microcapsules via ionic gelation methods, requiring no additional chemicals other than sodium alginate and calcium chloride, thereby allowing recognition of higher quantities of a template molecule, for example, as much as about 3 milligrams ("mg") of a template molecule, such bovine serum albumin (BSA), per gram of microcapsule. In some embodiments, the microcapsules of the present invention may be able to bind from about 0.75 mg to about 3 mg of a template molecule per gram of microcapsule. In some embodiments, the microcapsules of the present invention may be able to bind from about 1 mg to about 3 mg of a template molecule per gram of microcapsule. In some embodiments, the microcapsules of the present invention may be able to bind from about 2 mg to about 3 mg of a template molecule per gram of microcapsule.

Ionic gelation generally refers to the process of formation of three dimensional ties/connections/junctions from macromolecular (polymer) chains by partial or total interaction of ionic charges, for example, positive ions and negative ions existing on the macromolecular chains or on branches, tethers and other molecular associations of the chains. Methods according to some embodiments of the invention may provide the release of the template molecule in as little as, for example, about 5 hours.

In addition to being rapid and facile, methods of the present invention also may produce microcapsules with substantially uniform pores and readily controlled size. The preparation process may be easily implemented and may take much less time than other, traditional polymerization methods. In some embodiments, the particle size may be controlled by varying the viscosity of the liquid used to form the microcapsules.

Figure 11:
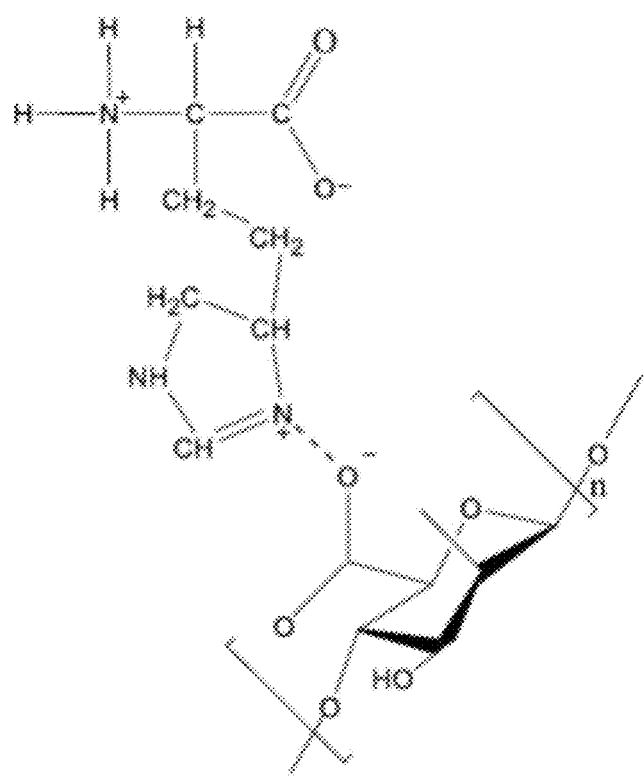
FIG. 11 shows the proposed ionic bond between histidine (an abundant amino acid in BSA) and alginate during the imprinting process.
Figure 12:
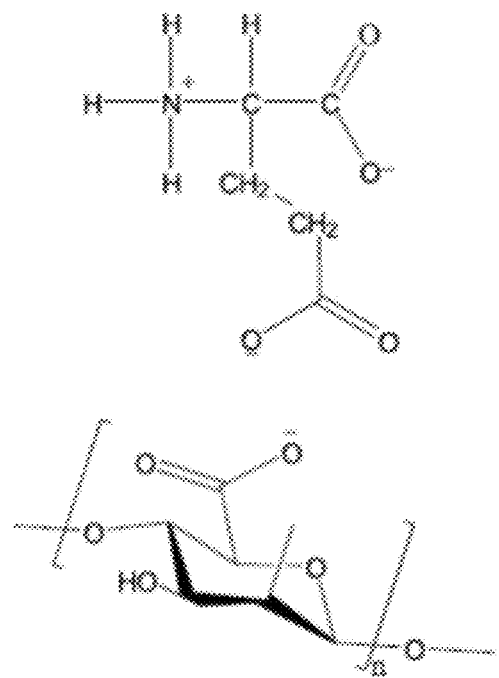
FIG. 12 shows the proposed repulsion between glutamic acid (an abundant amino acid in BSA) and alginate during the extraction process.

Without limiting the invention to a particular theory or mechanism of action, it is nevertheless currently believed that sodium alginate has hydroxyl and carbonyl groups that allow dipole/dipole interaction and hydrogen bonding between alginate and a template molecule. After crosslinking between sodium alginate and $Ca^{2+}$ ions, template molecules may be trapped inside the network and can be subjected to template removal and rebinding studies. To achieve good templated microcapsules, it may be preferred to bond the negatively charged carbonyl groups of alginate to the template molecule. For example, when the template molecule is BSA, it may be preferred to work below the isoelectric point of BSA (pI~4.7) to allow the BSA to behave as positively charged and favor a stronger attractive electrostatic interaction between the BSA (positively charged) and the alginate (negatively charged). Similarly, when the template molecule is BSA, a solution comprising BSA may be prepared with a pH adjusted to about 4.2 by hydrochloride solution. The alginate imprinted polymers described herein anticipates the non-covalent binding of the carboxyl group of the alginate polymer with the template molecule functional groups. The low pH of the solution during the crosslinking, which is below the pI of BSA, creates a positively charged, hydrophilic molecule, which non-covalently interacts with the anionic alginate. In the case of BSA, at a pH of 4.2 ionic interactions may occur between the alginate and histidine, as shown in FIG. 11. Raising the pH above the pI of BSA will cause a repulsion effect between the negatively charged BSA and the negatively charged alginate and break the ionic interactions, as shown in FIG. 12 for glutamic acid. Alginate may also form hydrogen bonds with a template molecule, which will be unaffected by the modulations in pH.

Thus, methods of protein imprinting based on calcium alginate polymer microcapsules, via ionic gelation, requires only two reactants: sodium alginate and calcium chloride, and may provide imprinting technology to new life-based applications. Furthermore, these methods may provide time savings, in regard to the preparation of microcapsules, since the preparation time decrease significantly with respect to the traditional polymerization methods.

Figure 1:
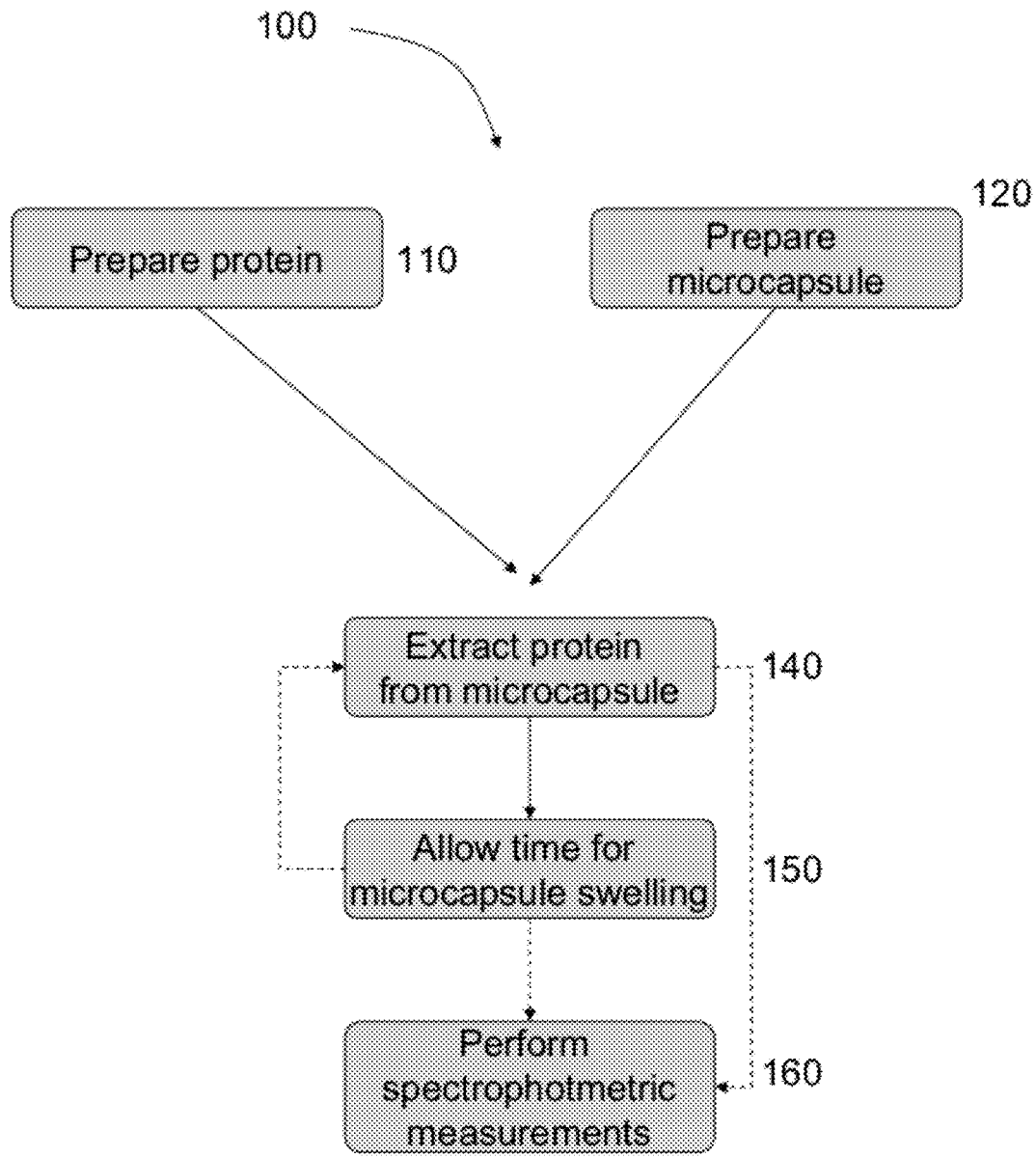

As illustrated in FIG. 1, in one embodiment, a method of the present invention 100 may comprise preparing or providing a template molecule, such as a peptide or a protein 110. The method 100 may further comprise forming a microcapsule comprising calcium alginate 120 (which may precede, follow, or occur substantially simultaneously with preparing or providing a template molecule). For example, in one embodiment forming a microcapsule comprising calcium alginate may comprise the addition of an amount of sodium alginate to the template solution to achieve a desired concentration, followed by dropwise addition into a calcium chloride aqueous solution to obtain a template imprinted microcapsule 120. The method may further comprise an additional step of removing the template molecule from the microcapsule 140. Complete extraction of the template molecule from the microcapsule may further require allowing time for microcapsule swelling 150. In some embodiments, removing the template molecule from the microcapsule 140 and allowing time for microcapsule swelling 150 may be successively repeated. Optionally, in some embodiments, the imprinted microcapsules may then be used to recognize the template molecule. Either as a quality verification mechanism, or as a part of recognizing a target molecule, spectrophotometric measurements of the microcapsules may be performed 160.

In contrast to previous work done on protein imprinting based on alginate microcapsules, which typically removed a BSA template molecule in about 48 hours through successive washes and agitation (discontinuous procedure), some embodiments of the present invention achieve a release of between about 87 and about 90% of the template molecule in only about 5 hours by combining discontinuous and continuous procedures. For example, see the results presented in FIGS. 2 and 3. Removal of the template molecule from the microcapsules may proceed by breaking the bonds between the template molecules and the alginate chains. For example, the microcapsules may be washed using an elution solution. In some embodiments, the elution solution may include calcium. For example, such a solution may comprise a mixture of about 1.0 wt. $CaCl_2$ and Tris buffer solution (about 0.05 M, pH of about 7.4). Tris Base buffer solution may be commercially available from ThermoFisher Scientific, Inc. of Waltham, Mass. It is believed that, due to the mechanism of formation of microcapsules by ionic gelation, the membrane of the microcapsules may grow from outside to inside by diffusion of cations of calcium throughout the membrane. A pH of about 7.4 may force the BSA to behave as negatively charged molecules, thus reducing the interactions between BSA and the negatively charged matrix of alginate. As has been shown in "Proteins incorporated into biomimetically prepared calcium phosphate coatings modulate their mechanical strength and dissolution rate," by Liu et al. (*Biomaterials* v 24, pp 65-70, 2003), the calcium of the elution solution may interact with the template molecule and may force the template molecule to diffuse out the microcapsules.

After removal of the template molecule, the microcapsules may be stored in deionized water in a refrigerated environment (e.g., from about 4 to about 8° C.) for a period of time to allow the swelling process of the microcapsules. This time period may be a time sufficient to achieve a weight that does not change within about 0.05%, for example, from about 48 to about 96 hours). This may also permit the recovery of the original size of the microcapsules in the rebinding process, since the process of removal of the template molecule may cause the thickness of the membrane of the microcapsules to increase, and therefore may reduce the interior space inside the microcapsules, thereby reducing the space available inside the microcapsules to accommodate the template molecule again in the rebinding process.

Figure 2:
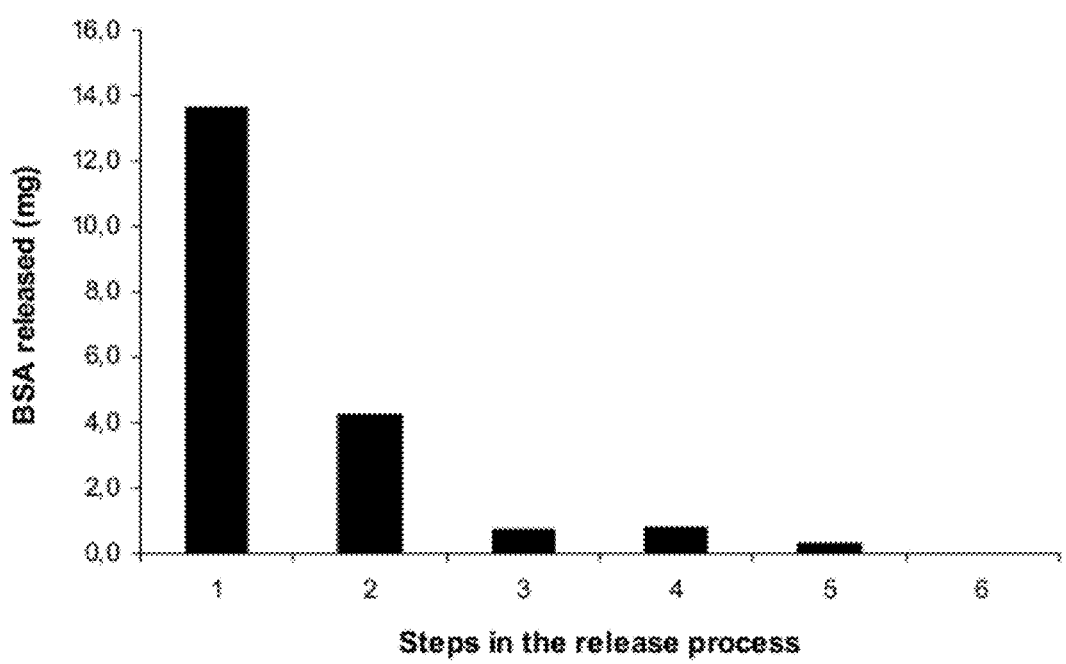
Figure 3:
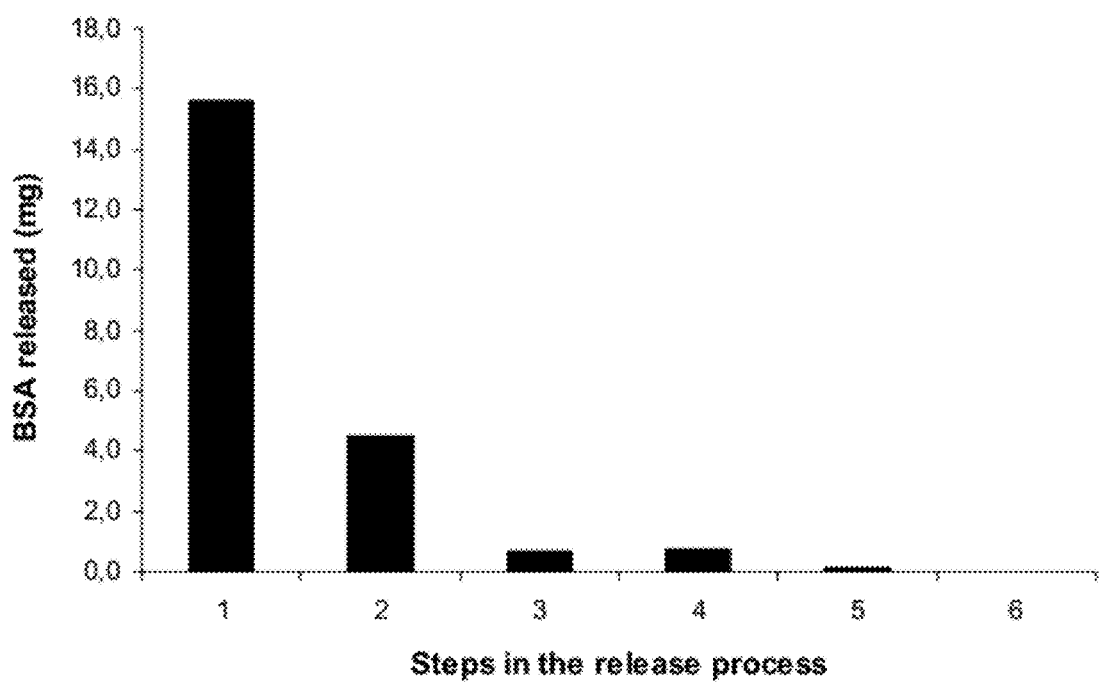
Figure 4:
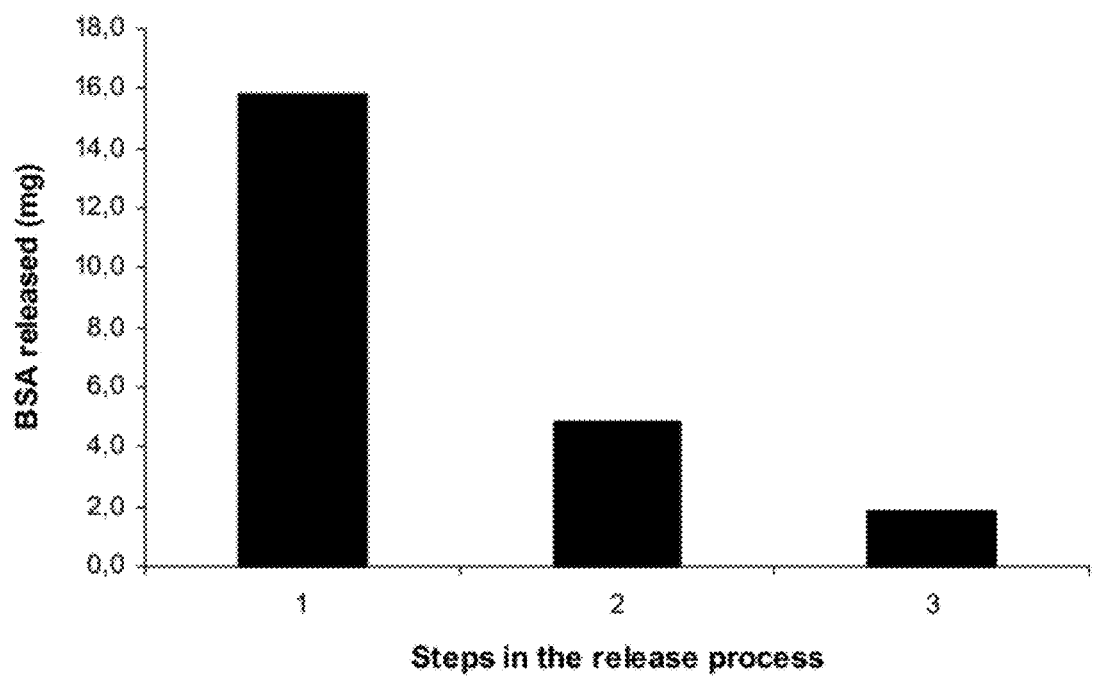
Figure 5:
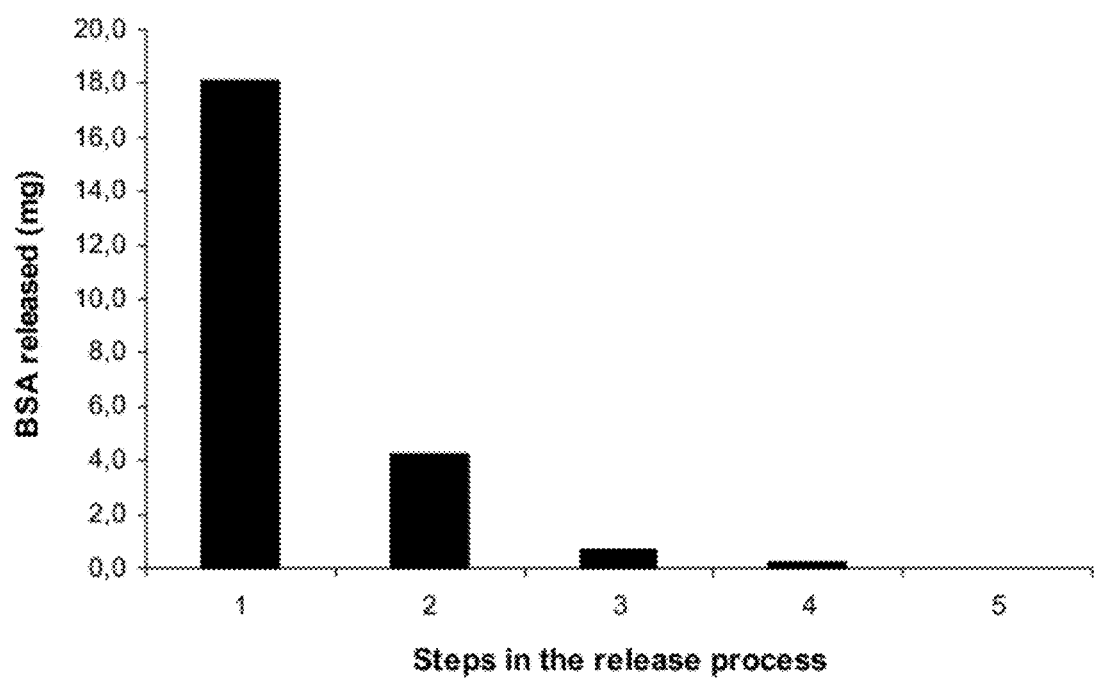

In some embodiments of the invention, total release of the template molecule from the microcapsules may require more than five hours. For example, see the results illustrated in FIG. 4. It is believed that this may be due to the three cycles of mixing-extraction, the last taking place overnight. This may be undesirable; because of the calcium of the elution solution may create thicker microcapsule membranes with the greater time, which may result in not enough space inside of the microcapsules to achieve the rebinding process. Therefore, in some embodiments, releasing the template molecule may comprise only two cycles of washing and maintaining the microcapsules in deionized water during 5 days, wherein the water is renewed daily by filtering. For example, see the results illustrated in FIG. 5. This may provide for the swelling process, while allowing the release of the remaining amount of template molecule without the presence of calcium. Since it is not necessary to achieve total release of the template molecule to attain a satisfactory recognition results, it may be preferable to use the removal process as illustrated in FIGS. 2 and 3 to save time and allow enough space in the inside of the microcapsules for the rebinding process. In some embodiments, at least about 75 to about 99% of the template molecule must be removed by washing so that the ensuing microcapsules can recognize it back.

As an optional step, recognition of the template molecule may be verified through tests, such as spectrophotometer measurements. Without limiting the invention to a particular theory or mechanism of action, it is nevertheless currently believed that, since the calcium alginate microcapsules are biodegradable, they may disintegrate over time. Therefore, in some embodiments, filtration of the supernatant may occur before considering final results of absorbance for recognition of the protein. As has been shown in "Facile synthesis of polyanilinesodium alginate nanofibers," by Yu et al. (*Langmuir*, v 22, pp 3899-3905, 2006), alginate generally absorbs at about 280 nm. Additionally, the tests of alginate absorption may be followed by tests of control microcapsules.

In other embodiments, the methods of the present disclosure may be used to synthesize molecularly imprinted alginate films. Such films can be incorporated, for example, into biomolecular sensors. In certain embodiments, when BSA is used as a template molecule, there is improved binding of BSA to the imprinted film, as compared results using an aqueous imprinting method. In other embodiments, proteins varying in charge and size may be equilibrated with the imprinted alginate films to elucidate the mechanism of binding interaction. In other embodiments, the methods of the present disclosure may be used to synthesize a molecularly imprinted product. In certain embodiments, the product is a microcapsule or a film.

To facilitate a better understanding of the present invention, the following examples of certain aspects of some embodiments are given. In no way should the following examples be read to limit, or define, the scope of the invention.

EXAMPLES

Example 1

Calibration of the Protein

A calibration absorbance/concentration was carried out in order to determine the concentration with time of the protein by means of spectrophotometer measurements.

Figure 6A:
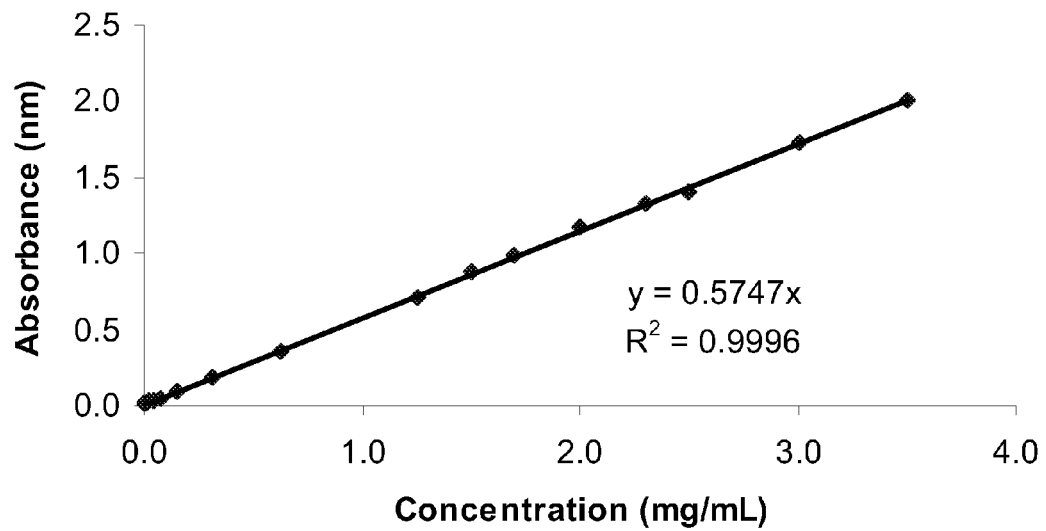
FIGS. 6A and 6B illustrate calibration curves to BSA.
Figure 6B:
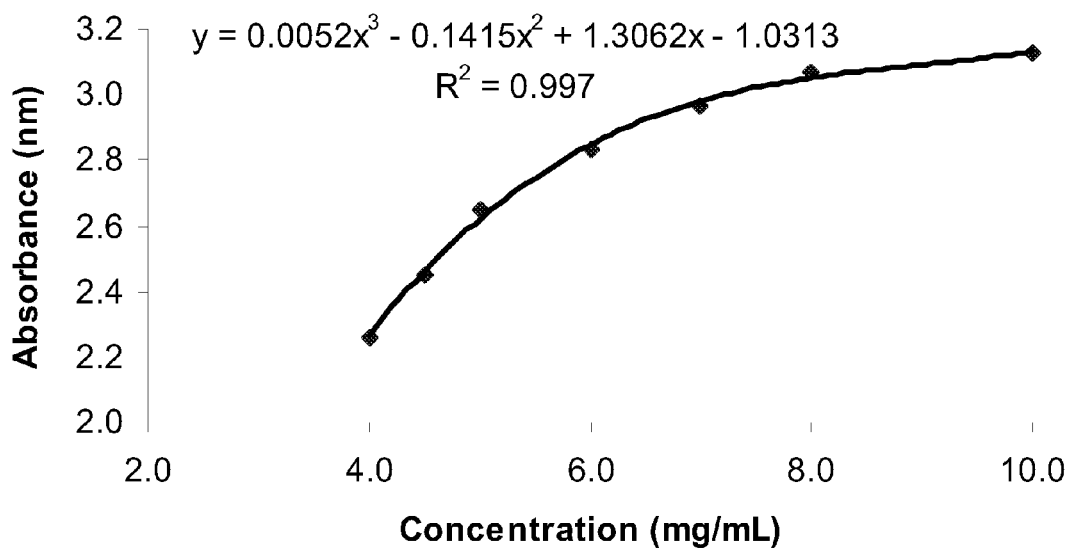

Calibration was based on about 20 mL of an about 10 mg/mL protein solution as an initial solution. Different volumes (Table 1) were taken from the initial solution, to obtain different known concentrations of protein, and were disposed in micro centrifuge tubes, and all volumes were filled with deionized water until reaching about 1.5 mL. FIG. 6 show the calibration graphs.

TABLE 1

| V, µL | 1500 | 1200 | 1050 | 900 | 750 | 675 | 600 | 525 | 450 | 375 | 345 | 300 |
|---|---|---|---|---|---|---|---|---|---|---|---|---|
| Conc., mg/mL | 10.0000 | 8.0000 | 7.0000 | 6.0000 | 5.0000 | 4.5000 | 4.0000 | 3.5000 | 3.0000 | 2.5000 | 2.3000 | 2.0000 |
| V, µL | 255 | 225 | 187.50 | 93.75 | 46.88 | 23.44 | 11.72 | 5.86 | 2.93 | 1.47 | 0.73 | |
| Conc., mg/mL | 1.7000 | 1.5000 | 1.2500 | 0.6250 | 0.3125 | 0.1563 | 0.0782 | 0.0391 | 0.0195 | 0.0098 | 0.0049 | |

Example 2

Generation of BSA-Embedded Molecular Imprinted Calcium Alginate Microcapsules BSA was dissolved in deionized water (with pH adjusted to about 4.2 by hydrochloride solution) until reaching a concentration of about 10 mg BSA/mL. Then, sodium alginate powder was added in the BSA solution until reaching a concentration of about 2% wt. For example, suitable sodium alginate powder may be commercially available from SIGMA-ALDRICH® of St. Louis, Mo.

After the preparation of the solution, about 3 mL of the mixture was added dropwise into an about 2% wt. (alternatively about 0.5 to about 8% wt. may be used) calcium chloride aqueous solution, thereby forming microbeads. For example, suitable calcium chloride may be commercially available from EMD Chemicals, Inc. of Madison, Wis. (calcium chloride dehydrate OmniPur Reagent Grade). The microbeads were kept in the cross-linking solution for about 2 minutes (alternatively from about 5 to about 30 minutes, preferably from about 1 to about 10 minutes, preferably from about 1.5 to about 5 minutes). The microbeads were collected by filtration with a nylon filter membrane of about 0.2 microns.

A sample of the supernatant was taken and analyzed to measure the loss in the whole process of the generation of the microcapsules. To know the exact weight of the microcapsules, a syringe was weighed before and after the generation of the microcapsules.

The microbeads were then placed in a reactor for the procedure of releasing of the protein.

Also, microcapsules without the protein (BSA) were prepared for non-imprinted (NIP) control samples. The procedure was the same as above. For the production of the NIP and control microcapsules, a specific amount of sodium alginate powder was dissolved into deionized water to form an about 2% wt solution.

Example 3

Generation of Drops by Means of Extrusion

The solution (a mixture of alginate and the aqueous solution of protein) was extruded drop by drop through a needle using a sterile syringe into the calcium chloride gelation solution under stirring. This technique generated microcapsules with a particle size ranged between about 2 to about 3 mm. Note, that it is possible to control the particle size by varying the liquid viscosity. The alginate solution's viscosity may be varied by changing the alginate solution concentration, which may be used to control the size of the capsules.

Example 4

Removal of the Template

Tris Buffer powder was dissolved in deionized water to achieve a Tris buffer solution of about 0.05 M. The pH of the buffer solution was set at about 7.4 by adding Hydrochloric Acid 1 N. For example, suitable Hydrochloric Acid 1 N may be commercially available from ThermoFisher Scientific, Inc. of Waltham, Mass. Next, calcium chloride powder was added in the Tris solution until reaching a concentration of about 1% wt.

Figure 7:
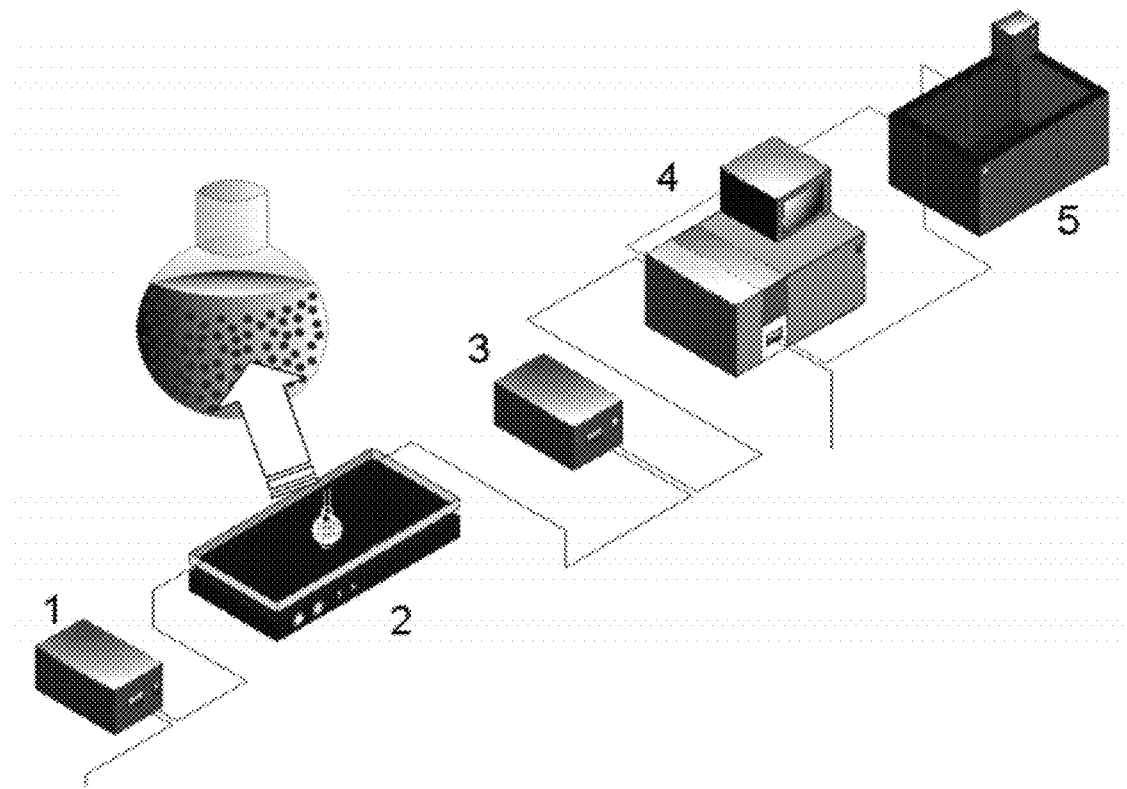
FIG. 7 illustrates equipment used to the remove the template molecule. For example, (1) and (3) peristaltic pumps; (2) reactor over an orbital shake rotator; (4) spectrophotometer that operates in continuous; (5) thermostatic bath.
Figure 8A:
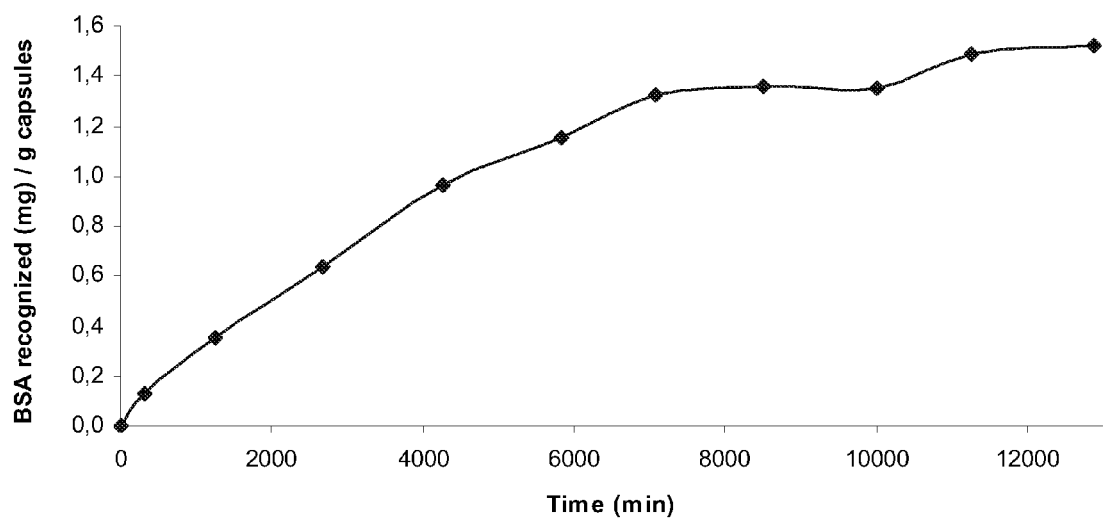
FIGS. 8A and 8B illustrate recognition studies.
Figure 8B:
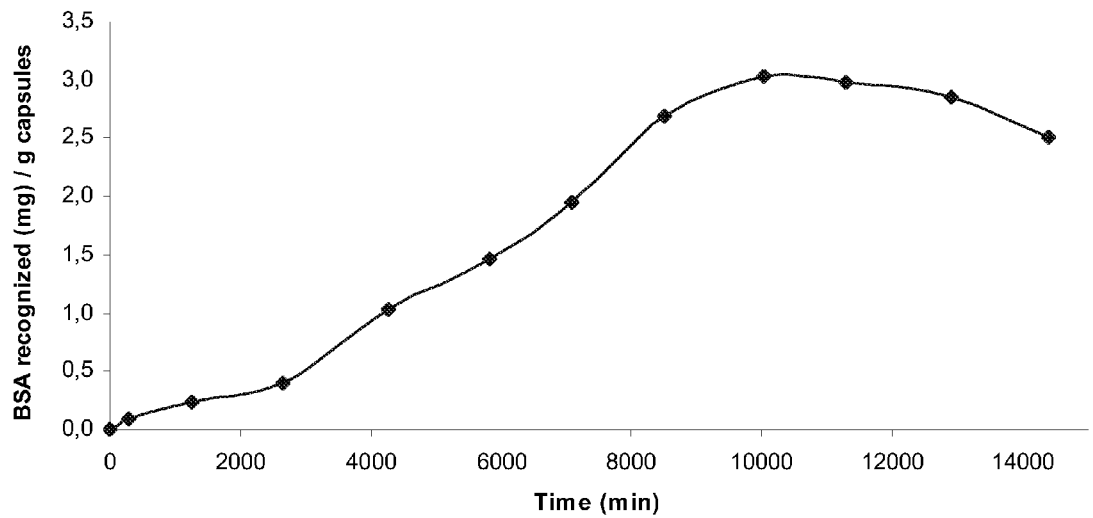
Figure 9:
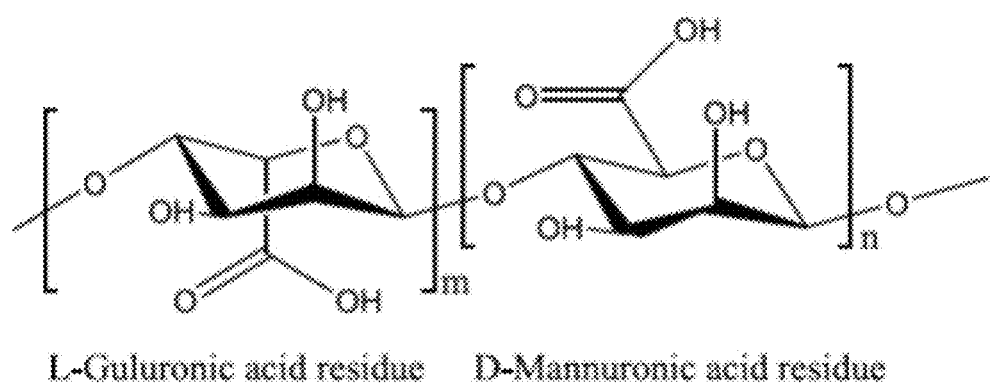
FIG. 9 shows the chemical structure of alginate.
Figure 10:
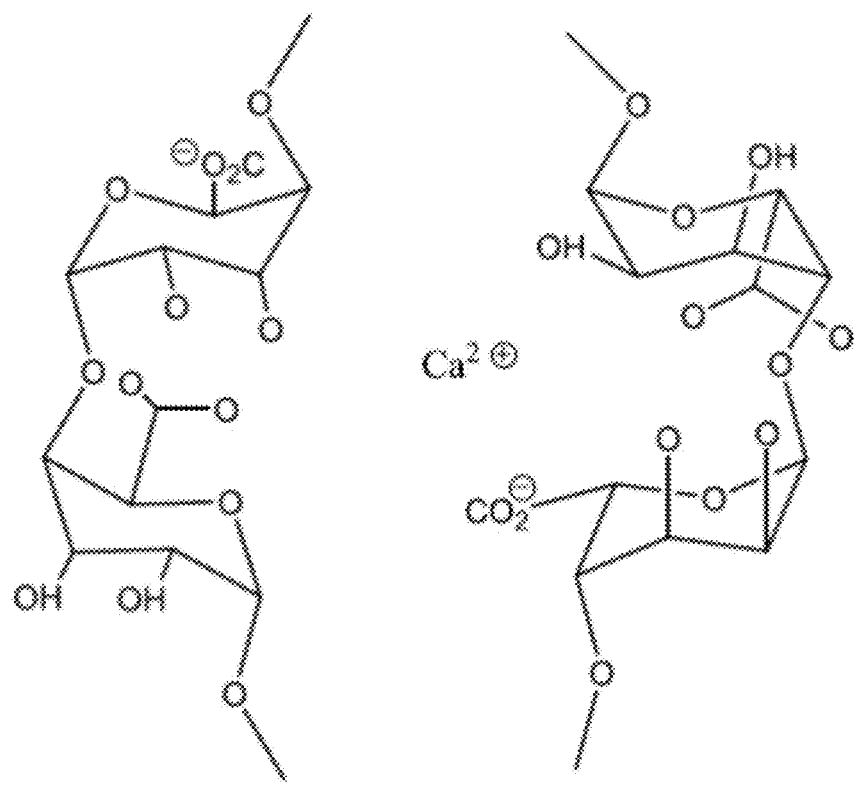
FIG. 10 shows the coordination of alginate chains with divalent calcium.

The microcapsules were placed in a beaker containing the elution solution: a mixture of about 1.0 wt. $CaCl_2$ and Tris buffer solution (about 0.05 M, pH of about 7.4). The samples were briefly agitated. Then, the washing buffer was renewed by means of a continuous system until no additional template could be removed with this process (absorbance zero). An illustration of the system is shown in the FIG. 7. After that, the whole process was repeated (mixing and continuous system). Finally, the process was repeated the last time, reducing the time of the mixing process. In some examples, the optimum stirring time may be between about 1.5 hours to about 2 hours, and the cycle time of agitation may be reduced down to about 30-40 minutes of agitation in the last cycle.

After the removal process of the templates, the microcapsules were stored in a refrigerated environment (e.g., about 4-8° C.) for several days (e.g., 2 days may be sufficient to allow the process of swelling that will provide enough space inside of the capsules to achieve the rebinding process) in deionized water to allow the swelling process of the microcapsules. During this time, besides producing the swelling process, any remaining amount of template was released. The deionized water was changed daily by filtration, and the supernatant was analyzed to know the release of the remaining amount of template.

The NIP and control microcapsules were subjected to the same process to maintain the same conditions that the MIP microcapsules.

Example 5

Recognition of the Protein

A specific amount of BSA was dissolved in deionized water until reaching a concentration of about 1 mg BSA/mL. An accurately weighed amount of wet microcapsules (using filter paper to absorb the surface water) was placed in a centrifuge tube with about 40 mL of the about 1 mg/mL protein solution. The concentration of protein was evaluated with time by absorbance at about 280 nm using a spectrophotometer. The detection was continued until the change in concentration of the solution was undetectable, and the equilibrium rebinding capacity was obtained.

The process was repeated with the microcapsules without the protein, NIP, and the control microcapsules. The procedure was the same as above.

The results were compared for the MIP and NIP microcapsules, providing an estimate of the amount of protein recognized. The control microcapsules were used to know the absorbance of the alginate with time. For experiments with control microcapsules, microcapsules without protein were placed in just deionized water. The results are presented in Tables 2 and 3.

TABLE 2

| | MIP BSA adsorption | NIP | MIP − NIP (mg)/mg capsules |
|---|---|---|---|
| Time | (mg BSA/g caps) | (mg BSA/g caps) | (recognition) |
| 0 | 0.0000 | 0.0000 | 0.0000 |
| 5 h 7' | 1.7368 | 1.6046 | 0.1322 |
| 20 h 50' | 2.2868 | 1.9360 | 0.3508 |
| 44 h 25' | 3.4940 | 2.8613 | 0.6326 |
| 71 h 17' | 4.6000 | 3.6389 | 0.9611 |
| 97 h 0' | 5.5428 | 4.3863 | 1.1565 |
| 118 h 14' | 6.5308 | 5.2050 | 1.3258 |
| 141 h 58' | 7.4516 | 6.0903 | 1.3613 |
| 167 h 2' | 8.3031 | 6.9564 | 1.3467 |
| 187 h 55' | 9.1284 | 7.6417 | 1.4867 |
| 215 h 00' | 9.8151 | 8.2950 | 1.5200 |

TABLE 3

| | MIP BSA adsorption | NIP | MIP − NIP (mg)/g capsules |
|---|---|---|---|
| Time | (mg BSA/g caps) | (mg BSA/g caps) | (recognition) |
| 0 | 0.0000 | 0.0000 | 0.0000 |
| 4 h 52' | 0.9024 | 0.8078 | 0.0945 |
| 20 h 50' | 2.3644 | 2.1210 | 0.2434 |
| 44 h 20' | 3.4763 | 3.0751 | 0.4012 |
| 71 h 9' | 4.7453 | 3.7179 | 1.0274 |
| 97 h 0' | 5.8790 | 4.4105 | 1.4685 |
| 118 h 14' | 6.9889 | 5.0367 | 1.9522 |
| 141 h 58' | 8.4829 | 5.7887 | 2.6941 |
| 167 h 2' | 9.5215 | 6.4954 | 3.0261 |
| 187 h 55' | 10.2306 | 7.2540 | 2.9766 |
| 215 h 0' | 10.7398 | 7.8807 | 2.8591 |
| 239 h 37' | 11.0757 | 8.5693 | 2.5064 |

Example 6

Gelation of Alginate MIPs

Molecularly imprinted alginate hydrogel films were prepared by cross-linking sodium alginate in the presence of the template protein, bovine serum albumin (BSA). Deionized (DI) water was titrated to a pH of 4.2 with HCl (Fisher Scientific). To form the imprinting solution, 200 mg BSA (Sigma-Aldrich) was dissolved in 20 ml DI water at pH 4.2. Next, 0.4 g sodium alginate (Sigma-Aldrich) was added and stirred until dissolved. To form the control solution, 0.8 g sodium alginate was added to 40 ml DI water at pH 4.2 and stirred until dissolved. Solutions were stored at 4° C. until use.

To cross-link films, 1.5 g of the alginate solutions was dispensed into a Petri dish with a 5-cm diameter. The solution was leveled, and then 5 ml of an aqueous 2% calcium chloride ($CaCl_2$) (Fisher Scientific) solution was pipetted over the alginate. The alginate was allowed to cross-link for 4 min.

Upon exposure to the divalent $CaCl_2$ solution, a semi-opaque, mechanically stable film quickly formed. This film could be transferred with tweezers to the Tris buffer rinse solution upon completion of the cross-linking. The thickness of the resulting films was approximately 1 mm.

Example 7

Release of Template from Alginate MIP

After cross-linking, the films were rinsed and the release of BSA from the alginate rinse solutions was monitored. First the films were rinsed in a 0.05 M Tris-HCl (pH 7.4) solution with 1% $CaCl_2$, which was changed hourly for 3 h, and then the films were rinsed in DI water. The water was changed daily until a sample of the rinse solution had an absorbance<0.003 OD, as measured at 280 nm on a Lambda 10 UV-Vis spectrophotometer (Perkin Elmer). A calibration curve developed from a serial dilution of a 1 mg/ml solution of BSA was used to calculate the amount of BSA in each rinse solution.

The release of BSA from the rinse solutions is shown in FIG. 13. Consistently, approximately 10 mg BSA was detected in the rinse solutions, while 15 mg BSA was in the polymer solution prior to cross-linking. A significant portion of the BSA is likely removed during the cross-linking process, since cross-linking induces significant de-swelling of the gel. As the solvent is expelled from the polymer when it crosslinks, the template molecule is also pushed out of the film.

Example 8

Recognition of Alginate MIP

Recognition studies were performed by incubating cross-linked and rinsed alginate films with BSA solutions. A 1 mg/ml solution of BSA in deionized water was prepared, and 50 ml of the solution was added to a 50 ml polypropylene centrifuge tube with the alginate film. The samples were placed on a rotary mixer and the solution was sampled daily to read the absorbance of the solution at 280 nm using a UV-Vis spectrophotometer (Lambda 10, Perkin Elmer) until equilibration was reached. To calculate the absorption of BSA at equilibrium, equation (1) was used:

$$Q_e = \frac{(C_0 - C_{eq})V}{W} \quad (1)$$

where $Q_e$ is the equilibrium absorption, $C_0$ is the initial protein concentration, $C_{eq}$ is the final concentration of protein at equilibrium, V is the volume of the protein solution and W is the weight of the polymer incubated in the solution. Imprinting efficiency, IE, can then be defined as shown in equation (2):

$$IE = \frac{Q_{MIP}}{Q_{NIP}}. \quad (2)$$

The interaction between an imprinted polymer and the template molecule can be compared to an antigen-antibody binding interaction. This association and dissociation of the complex can be symbolized as:

$$[P] + [L] \underset{k_r}{\overset{k_f}{\rightleftarrows}} [PL]. \quad (3)$$

where [P] is the concentration of unbound antibody, [L] is the concentration of unbound ligand, [PL] is the concentration of protein and ligand which are bound, $k_f$ is the forward reaction rate and $k_r$ is the reverse reaction rate of association. A standard metric for the assessment of the strength of this interaction is the dissociation constant, or $K_D$. One can also define the equilibrium binding constant, $K_{eq}$, as shown in equation (4):

$$K_{eq} = \frac{k_f}{k_r} = \frac{1}{K_D} = \frac{[PL]}{[P][L]}. \quad (4)$$

The dissociation constant was used to compare the strength of the interaction between the polymer film and the template molecule with traditional antibody-antigen interactions. In our case, [P] becomes the concentration of possible binding sites in the polymer film, [L] is the concentration of template in solution and [PL] is the concentration of template absorbed and presumably bound in the polymer film, all observed at equilibrium.

Preferential absorption of the imprinted BSA template was demonstrated through equilibrium recognition studies. The calculated values for Qe (in units of mg/g polymer) are shown in Table 4. The amount of BSA absorbed was 6.4 mg/g polymer, which compares favorably to previously reported values of approximately 0.3 mg/g polymer. Using the equation for the dissociation constant, the $K_{eq}$ of the BSA imprinted alginate polymer was found to be 6 mM. This is several orders of magnitude above the dissociation constants found for small molecule imprinted polymers, and above the reported binding affinity of an epitope approach to BSA imprinting, which indicates a weaker interaction between the polymer matrix and the protein. However, these results are similar to the results of polymeric imprinting BSA in aqueous media, which have demonstrated adsorption capacities on the order of 5 mg/g polymer, and surface imprinted microbeads, with demonstrated adsorption capacities of 1.4 mg/g polymer. The absorption of BSA is shown as a function of time in FIG. 14. A single replicate (FIG. 14b) attains equilibrium within 6 days. Since the recognition experiment occurred in water, $Ca^{2+}$ ions will be exchanged and the film will slowly degrade, causing the loss of recognition sites for BSA over time. This gradual degradation accounts for the decrease in absorption of BSA at longer time points. The time to reach equilibrium varied between 3 and 6 days.

TABLE 4

Qe of alginate films imprinted for BSA (MIP) and non-imprinted (NIP), average of four recognition experiments(n = 3 for each experiment)

| Sample | $Q_e$ (mg/g polymer) | Imprinting Efficiency (IE) |
|---|---|---|
| MIP | 6.4 | 64 |
| NIP | 0.1 | — |

Example 9

Specificity of Alginate MIP

Proteins with varying molecular mass and isoelectric points (pI), provided in Table 5, were selected for determining the specificity of the alginate MIP for BSA (all proteins obtained from Sigma-Aldrich). Ovalbumin is a protein found in abundance in egg white, with a pI similar to BSA but with a lower molecular mass. It is expected that ovalbumin would bind non-specifically to any cavities formed in the BSA-imprinted films. Hemoglobin (Hb) is the oxygen-transporting protein found in red blood cells. The bovine hemoglobin selected for these experiments has a molecular mass similar to BSA, but with a higher pI. In water, Hb should be close to neutral in charge. Human serum albumin (HSA) has a similar molecular mass and pI, but a different structure from that of BSA.

Alginate hydrogels used in the selectivity experiments were prepared as described above. Films were then incubated in 1 mg/ml solutions of the competitor proteins selected and the absorbance of each solution was measured daily. The absorbance of the ovalbumin solutions were read on the Lambda 10 UV-Vis spectrophotometer in a cuvette at 280 nm. The absorbance of the Hb solutions was read on the same spectrophotometer at 405 nm. The absorbance of the HSA samples was read using a microplate reader (Synergy HT, Biotek) at a wavelength of 280 nm.

To analyze the selectivity of the alginate hydrogels for the template protein, the selectivity, $\alpha$, was calculated using equation (5):

$$\alpha = \frac{K_{a,template}}{K_{a,competitor}}, \quad (5)$$

where the equilibrium affinity constant is calculated using equation (4).

TABLE 5

Molecular Mass and Isoelectric Points of Proteins Used In the Selectivity Studies

| Protein | Molecular Mass (kDa) | pI | Hydrodynamic radius (Å) |
|---|---|---|---|
| BSA | 66 | 4.9 | 120 |
| Ovalbumin | 45 | 4.7 | 27.4 |
| HSA | 69 | 4.8 | 34.5 |
| Hb | 68 | 6.8 | 55 |

The results of the specificity experiments reveal that the imprinting efficiency of the BSA imprinted alginate films is significantly lower for the selected proteins than for the BSA itself, meaning that the amount protein absorbed by the MIP is similar to the amount of protein absorbed by the NIP for ovalbumin, Hb and HSA, as shown in Table 6. The selectivity of the films, calculated using equation (6), is insufficient for ovalbumin and Hb. In the case of ovalbumin, precipitation of the polymer occurred during the course of the experiment, making the standard specificity calculation inaccurate—a significant amount of the protein was simply precipitated out of solution, rather than absorbed into the imprinted alginate film. The imprinting efficiency results demonstrate this more clearly, in that the MIP does not absorb more OVA than the NIP. In the case of Hb, it is likely that the predominance of positively charged residues on the protein, at the pH under test, allows the Hb to non specifically bind to the anionically charged alginate. This experiment demonstrates that though the molecular imprinting appears to be a real effect, the application of the films in physiological conditions may be limited due to significant non-specific binding of positively charged species in physiological conditions.

TABLE 6

Selectivity Comparison (Films imprinted with BSA, exposed to either BSA or a competitive molecule (n = 3))

| Protein | α | IE |
|---|---|---|
| Ovalbumin | $1.6 \times 10^{-6}$ | 1.1 |
| Hb | $1.4 \times 10^{-7}$ | 1.0 |
| HSA | $-1.0 \times 10^{-5}$ | 1.1 |

Example 10

Swelling of Alginate MIP

Since the degree of swelling and, therefore, the pore size, of the alginate hydrogels may be affected by the imprinting process, the swelling of the films was monitored after synthesis. The cross-linked polymer films, imprinted as described above, using non-imprinted polymer films cross-linked without BSA as controls, were weighed immediately after synthesis. The films were incubated in deionized water, removed from the incubation solution each day, blotted to remove excess solvent and weighed.

The degree of swelling, Q, was calculated using equation (6):

$$Q = \frac{W_0 - W_t}{W_0}, \quad (6)$$

where $W_0$ is the as-synthesized initial weight, and $W_t$ is the weight at time t.

The swelling behavior of the imprinted alginate films was similar to that of the non-imprinted alginate films. As shown in FIG. 15, the MIP and NIP films present similar in the degree of swelling and swelling kinetics. The existence of similar swelling kinetics in both the imprinted and non-imprinted films indicates that the mesh size of the alginate films is sufficiently large that the presence of imprinted cavities within the film does not enhance the transport of solvent into the film, and the effect of the imprinting process upon the swelling behavior of the alginate films is minimal.

Thus, we have found that the binding of BSA to alginate films is comparable, and in some cases improved, over large macromolecular imprinted results previously cited in the literature. Although in the experiments presented here the equilibration was reached after 6 days, this is due to the considerable thickness of the films. If the films were reduced in thickness from 1 mm to 1 μm, the time scale should be reduced from days to minutes, as has been demonstrated with alginate microbeads. Reduction of the film thickness can be achieved through spincoating and other micro and nanofabrication techniques. Although the imprinted versus non-imprinted films absorb the competitive proteins equally, some proteins exhibit high degrees of non-specific binding to the alginate films. This is due to the ionic interactions between a positively charged molecule and the negatively charged alginate—despite the presence of binding cavities preferential for BSA, the bulk alginate attracts a considerable amount of Hb, which has a higher pI. In addition to a careful design of the functional interactions, it is clear from these results there must also be some consideration for avoidance of non-specific binding, perhaps by incorporation of poly(ethylene glycol) (PEG), which could shield the bulk polymer from non-specific binding. Little attention has been paid to this issue in literature, possibly since often these materials will be used for chromatography applications where the composition of the solution is more controlled in comparison to biomedical applications where the physiological environment is quite complex.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

1. Zhao, K., Cheng, G., Huang, J., Ying, X. (2008), "Rebinding and recognition properties of protein-macromolecularly imprinted calcium phosphate/alginate hybrid polymer microspheres", React. Funct. Polym. 68.732-741.
2. Luzinov, I. (2008), "Molecularly imprinted fibers with recognition capability". National textile center annual report. November 2008. NTC Project: C05/CL01.
3. Zhang, F. J., Cheng, G. X., Ying, X. G. (2006), "Emulsion and macromolecules templated alginate based polymer microspheres", React. Funct. Polym. 66. 712-719.
4. Yu, Y., Chen, S., Bian, C., Chen, W., Xue, G. (2006), "Facile synthesis of polyanilinesodium alginate nanofibers", Langmuir. 22. 3899-3905.
5. Ge, Y., Turner, A. P. F. (2008), "Too large to fit? Recent developments in macromolecular imprinting", Trends in Biotechnology. 26 (4). 218-224.
6. Zhang, F. J., Cheng, G. X., Gao, Z., Li, C. P. (2006), "Preparation of porous calcium alginate membranes/microspheres via an emulsion templating method", *Macromol. Mater. Eng.* 291. 485-495.
7. Liu, c., Ji, X., Zhao, K., Cheng, G. (2007), "Preparation of hydroxyapatite/Ca-alginate composite microspheres via inverse suspension crosslinked method", *J. Appl. Polym. Sci.* 104.2034-2038.
8. Zhao, K., Huang, J., Ying, X., Cheng, G. (2008), "Macromolecularly imprinted calcium phosphate/alginate hybrid polymer microspheres with the surface imprinting of bovine serum albumin in inverse-phase suspension", *J. Appl. Polym. Sci.* 109.2687-2693.
9. Zhao, K. Y., Kan, R H., Wei, J. F., Cheng, G. X., Chen, L. (2008), "Bovine serum albumin imprinted calcium phosphate/polyacrylate/alginate multi/hybrid polymer microspheres in inverse-phase suspension", *e-Polymers.* 100. 1-7.

What is claimed is:

1. A method comprising:
providing a first solution comprising a template molecule;
combining sodium alginate with the first solution to form a second solution:
combining calcium chloride with the second solution thereby forming a microcapsule comprising calcium alginate and the template molecule, wherein the first and second solution are free of organic solvents such that formation of the microcapsule is performed in the absence of organic solvents;
removing the template molecule from the microcapsule to form an imprinted microcapsule; and
retaining the imprinted microcapsule.

2. The method of claim 1 wherein combining calcium chloride with the second solution comprises extruding the second solution into the calcium chloride in a dropwise manner.

3. The method of claim 1, wherein the second solution does not comprise a surfactant.

4. The method of claim 1, wherein the second solution consists essentially of a template molecule and sodium alginate.

5. The method of claim 1, wherein the template molecule is a peptide or a protein.

6. The method of claim 1, wherein the template molecule is bovine serum albumin.

7. The method of claim 1, wherein the first solution has a pH between about 4.0 and about 4.5.

8. The method of claim 1, wherein removing the template molecule from the microcapsule comprises breaking bonds between the template molecule and the calcium alginate.

9. The method of claim 8, wherein breaking bonds between the template molecule and the calcium alginate comprises washing the microcapsules with an elution solution and allowing time for swelling of the microcapsules.

10. The method of claim 9, wherein the elution solution comprises calcium.

11. The method of claim 9, wherein the elution solution has a pH between about 7.2 and about 7.6.

12. The method of claim 9, wherein washing the microcapsules occurs for a period of time between about 1 and about 5 hours.

13. The method of claim 9, wherein allowing time for swelling of the microcapsules occurs for a period of time between about 1 and about 4 days.

14. The method of claim 9, wherein the microcapsules are immersed in deionized water while allowing time for swelling of the microcapsules.

* * * * *